(12) United States Patent
Ressemann et al.

(10) Patent No.: US 8,267,872 B2
(45) Date of Patent: Sep. 18, 2012

(54) STEERABLE GUIDE WIRE WITH TORSIONALLY STABLE TIP

(75) Inventors: Thomas V. Ressemann, St. Cloud, MN (US); Peter T. Keith, St. Paul, MN (US)

(73) Assignee: St. Jude Medical, Cardiology Division, Inc., Minnetonka, MN (US)

( * ) Notice: Subject to any disclaimer, the term of this patent is extended or adjusted under 35 U.S.C. 154(b) by 81 days.

(21) Appl. No.: 11/176,485

(22) Filed: Jul. 7, 2005

(65) Prior Publication Data
US 2007/0010762 A1    Jan. 11, 2007

(51) Int. Cl.
*A61B 5/00* (2006.01)
(52) U.S. Cl. ...................................................... 600/585
(58) Field of Classification Search .................. 600/585; 604/264, 523–284
See application file for complete search history.

(56) References Cited

U.S. PATENT DOCUMENTS

| | | | |
|---|---|---|---|
| 3,612,058 A * | 10/1971 | Ackerman | 600/585 |
| 4,579,127 A * | 4/1986 | Haacke | 600/585 |
| 4,682,607 A | 7/1987 | Vaillancourt et al. | |
| 4,763,647 A | 8/1988 | Gambale | |
| 4,867,173 A * | 9/1989 | Leoni | 600/585 |
| 4,932,419 A * | 6/1990 | de Toledo | 600/585 |
| 4,967,753 A * | 11/1990 | Haase et al. | 600/585 |
| 5,007,434 A | 4/1991 | Doyle et al. | |
| 5,063,935 A | 11/1991 | Gambale | |
| 5,144,959 A | 9/1992 | Gambale et al. | |
| 5,203,772 A * | 4/1993 | Hammerslag et al. | 600/585 |
| 5,228,453 A | 7/1993 | Sepetka | |
| 5,299,580 A | 4/1994 | Atkinson et al. | |
| 5,377,690 A * | 1/1995 | Berthiaume | 600/585 |
| 5,379,779 A * | 1/1995 | Rowland et al. | 600/585 |
| 5,542,434 A * | 8/1996 | Imran et al. | 600/585 |
| 5,769,796 A | 6/1998 | Palermo et al. | |
| 5,772,609 A | 6/1998 | Nguyen et al. | |
| 5,827,201 A | 10/1998 | Samson et al. | |
| 5,833,631 A | 11/1998 | Nguyen | |
| 5,902,254 A | 5/1999 | Magram | |
| 5,938,623 A | 8/1999 | Quiachon et al. | |
| 5,951,496 A | 9/1999 | Willi | |
| 6,017,319 A | 1/2000 | Jacobsen et al. | |
| 6,019,736 A | 2/2000 | Avellanet et al. | |
| 6,139,510 A | 10/2000 | Palermo | |
| 6,159,165 A | 12/2000 | Ferrera et al. | |
| 6,168,570 B1 * | 1/2001 | Ferrera | 600/585 |
| 6,183,420 B1 | 2/2001 | Douk et al. | |
| 6,190,353 B1 | 2/2001 | Makower et al. | |

(Continued)

FOREIGN PATENT DOCUMENTS

WO    WO 2005/016433    2/2005
(Continued)

*Primary Examiner* — Max Hindenburg
*Assistant Examiner* — John Pani
(74) *Attorney, Agent, or Firm* — Holland & Hart LLP

(57) ABSTRACT

A steerable guide wire includes a core wire having a proximal end and a distal end. A multi-filament bundle is affixed to the distal end of the core wire. An outer coil surrounds at least a portion of the core wire and the multi-filament bundle. A proximal end of the multi-filament bundle is secured to a distal end of the coil. By locating the multi-filament bundle in the distal tip portion of the guide wire, a guide wire is provided that is highly flexible, has a high degree of tensile integrity, and is highly steerable, even in tortuous vasculature.

5 Claims, 6 Drawing Sheets

U.S. PATENT DOCUMENTS

| | | |
|---|---|---|
| 6,344,029 B1 | 2/2002 | Estrada et al. |
| 6,383,146 B1 | 5/2002 | Klint |
| 6,428,489 B1 | 8/2002 | Jacobsen et al. |
| 6,440,088 B1 | 8/2002 | Jacobsen et al. |
| 6,488,637 B1 * | 12/2002 | Eder et al. .................... 600/585 |
| 6,579,246 B2 | 6/2003 | Jacobsen et al. |
| 6,579,278 B1 | 6/2003 | Bencini |
| 6,669,652 B2 | 12/2003 | Anderson et al. |
| 6,679,853 B1 | 1/2004 | Jalisi |
| 6,706,055 B2 * | 3/2004 | Douk et al. .................. 606/200 |
| 6,955,657 B1 * | 10/2005 | Webler ....................... 604/95.04 |
| 7,618,379 B2 | 11/2009 | Reynolds et al. |
| 2003/0069521 A1 | 4/2003 | Reynolds et al. |
| 2003/0181827 A1 | 9/2003 | Hojeibane et al. |
| 2003/0181828 A1 | 9/2003 | Fujimoto et al. |
| 2004/0039304 A1 | 2/2004 | Connors et al. |
| 2004/0054301 A1 | 3/2004 | Cassell et al. |
| 2004/0102719 A1 | 5/2004 | Keith et al. |
| 2004/0111044 A1 * | 6/2004 | Davis et al. .................. 600/585 |
| 2004/0143265 A1 | 7/2004 | Landry et al. |
| 2004/0193073 A1 | 9/2004 | DeMello et al. |
| 2004/0260206 A1 | 12/2004 | Murayama et al. |
| 2005/0027212 A1 | 2/2005 | Segner |
| 2005/0038359 A1 | 2/2005 | Aimi et al. |
| 2005/0080356 A1 | 4/2005 | Dapolito et al. |
| 2006/0064036 A1 | 3/2006 | Osborne et al. |

FOREIGN PATENT DOCUMENTS

| | | |
|---|---|---|
| WO | WO 2005/027212 | 3/2005 |
| WO | WO 2005/092422 | 10/2005 |

* cited by examiner

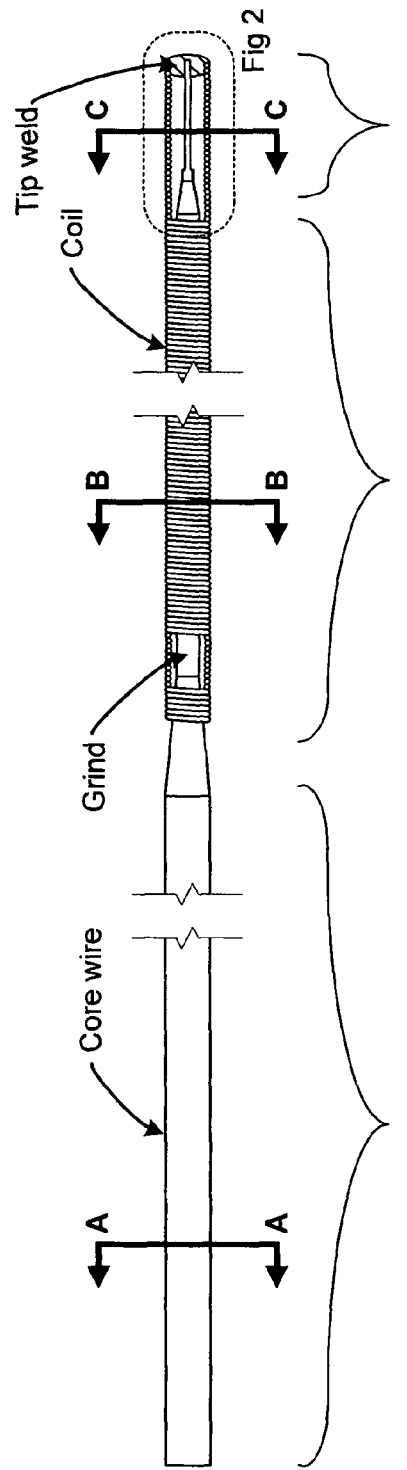
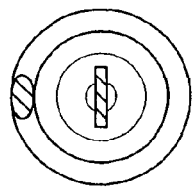
Section C-C
Fig. 1D (Prior Art)
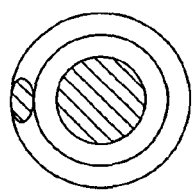
Section B-B
Fig. 1C (Prior Art)
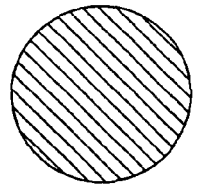
Section A-A
Fig. 1B (Prior Art)

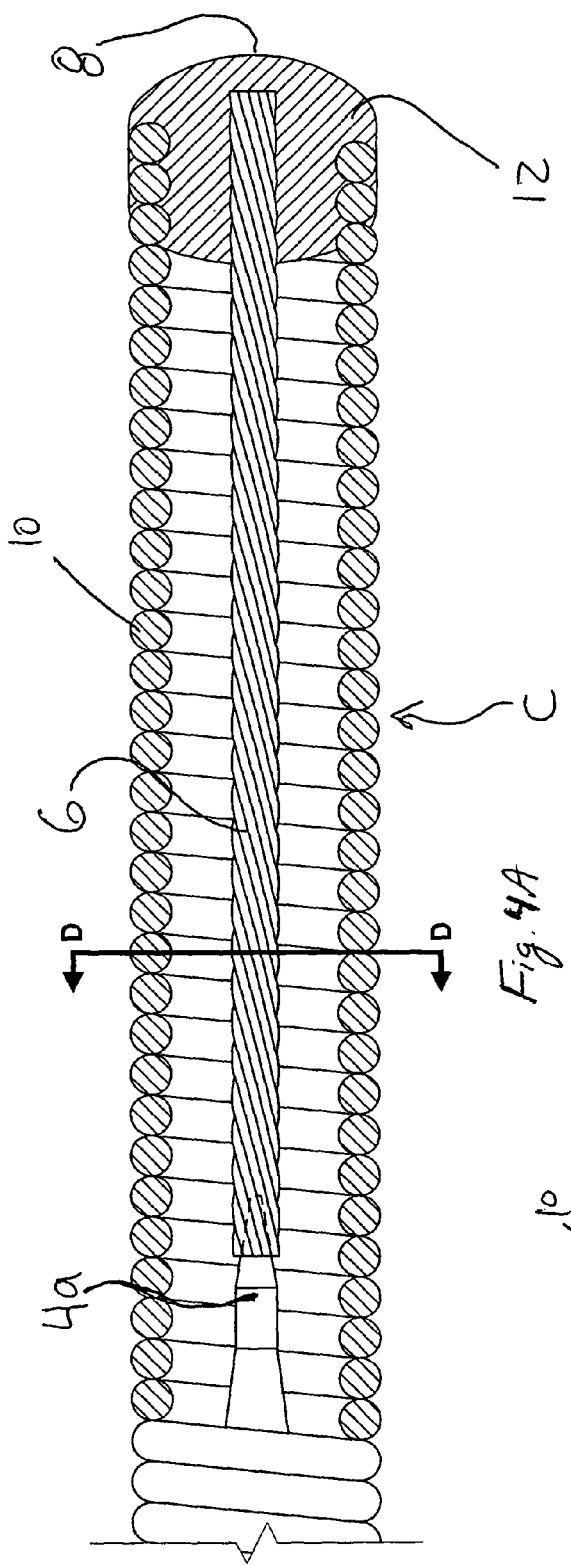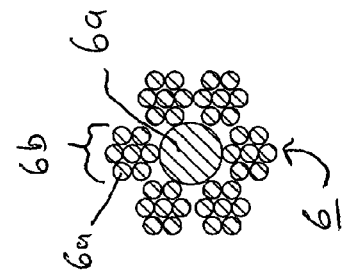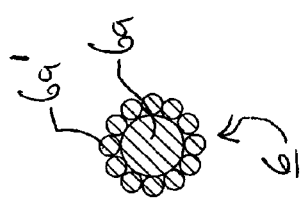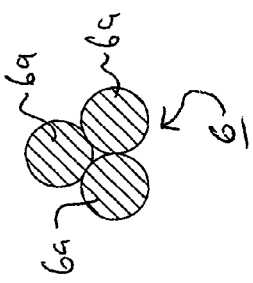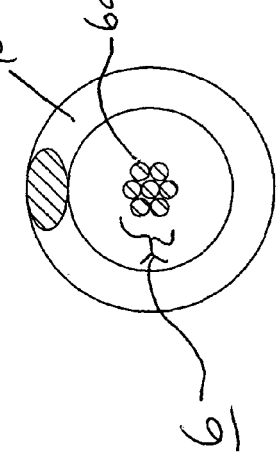

STEERABLE GUIDE WIRE WITH TORSIONALLY STABLE TIP

FIELD OF THE INVENTION

The field of the invention generally relates to guide wires. More particularly, the field of the invention relates to steerable guide wires used to access a site of interest inside a body lumen from a remote position located outside the body.

BACKGROUND OF THE INVENTION

Catheter based vascular interventions are becoming increasingly common in many of the vascular beds of the human body. For example, the treatment of obstructive plaque (e.g., stenosis) in coronary, peripheral, and cerebral arteries via angioplasty (with or without stents) has become a routine procedure. There remains a need, however, to improve the devices used in these procedures, to make them faster, easier, safer, and more viable, particularly in challenging anatomical situations.

The vast majority of catheter-based vascular interventions make use of a steerable guide wire to access the site of interest from a remote position outside the body. For example, in coronary interventions such as stent implantation, a steerable guide wire is advanced from the femoral artery access site into the various branches of coronary arteries and across the obstructive plaque. FIG. 5 illustrates the tip of a coronary guide wire accessing a coronary vessel with an obstructive plaque. After the guide wire is advanced past the stenosis, an interventional device such as a stent delivery balloon catheter (not shown) is advanced over the guide wire and through the stenosis. Thus, it is the guide wire that establishes the pathway for the interventional catheter that follows.

Steerability is an important performance characteristic for a steerable guide wire. Steerability generally refers to the ability to controllably rotate the distal tip of the guide wire to "point" the tip in the desired direction during the advancement procedure. Steerable guide wires typically have a "J" bend (for example, as seen in FIG. 5) imparted to the tip, either by the operator prior to the introduction into the body, or by the manufacturer. The ability to controllably orient this "J" bend allows the guide wire to be navigated into different branches of vessels and across the stenosis.

The ideal or optimum controllability of the tip of the guide wire is referred to as "1:1 torque response." This term refers to the ability of the tip to rotate exactly in step with rotation of the proximal end of the guide wire. For example, if the proximal end of the guide wire is rotated through 90 degrees, the tip will ideally rotate through 90 degrees—hence a 1:1 response.

Several factors influence the steerability qualities of a steerable guide wire. These include torsional stiffness of the guide wire components, dimensions, torsional modulus, guide wire straightness, guide wire resilience (ability to bend without plastically deforming), lubricity, and cross-sectional configuration. Steerability is also impacted by the tortuosity of the vascular anatomy.

Another important characteristic of a steerable guide wire is its tensile strength/integrity. This term generally refers to the guide wire's ability to withstand tensile forces applied to it without breaking. For example, the tips of guide wires occasionally get lodged in the stenosis or elsewhere in the vasculature, and when this happens it is important to be able to dislodge the tip by pulling on the proximal end of the guide wire. The design of prior art steerable guide wires has thus involved balance or trade-off between optimizing flexibility and steerability while at the same time maintaining tensile integrity.

FIGS. 1A-1D illustrates a typical construction of a prior art steerable guide wire, such as those commonly used in coronary interventions. As seen in FIG. 1A, the guide wire generally includes three portions, a proximal portion, a mid-portion, and a distal tip portion. There are two main components in steerable guide wires, a core wire that extends from a proximal end to a distal end, and a coil which extends over the mid-portion and tip portion of the guide wire. Lubricious coatings such as PTFE and/or hydrophilic or hydrophobic materials may also be present over some or all portions of the guide wire.

The core wire component of the guide wire is typically fabricated of high tensile strength stainless steel wire, however other materials are also used, such as NITINOL, MP35N, or ELGILOY. The guide wire is relatively stiff in the proximal portion and becomes increasingly more flexible towards the distal end. The proximal portion is typically of the original wire diameter (e.g., 0.014 inches for a coronary guide wire). The mid-portion is made more flexible by grinding down the diameter of the core wire to one or more smaller dimensions (e.g., 0.005 to 0.010 inches).

The distal tip portion of the guide wire is made even more flexible by further grinding of the core wire to a smaller dimension (e.g., 0.002 to 0.003 inches). While grinding the core wire to these smaller diameters does impart flexibility to the core wire, it is typically still not flexible enough for the tip portion to be atraumatic to the vasculature. Therefore the dimension of the core wire in the tip region is reduced even further by stamping or rolling the round wire into a flat ribbon configuration. The ribbon structure is illustrated in FIGS. 2A and 2B, as well as Section C-C in FIG. 1D. As seen in FIGS. 1D, 2A, and 2B, the ribbon is formed integrally with the core wire. However, in an alternative method of manufacture, it is also known to attach a separately formed piece of ribbon to a distal end of the mid portion of the core wire.

The high degree of flexibility achieved by the ribbon configuration could theoretically be accomplished by grinding the core wire to a round dimension that gives the equivalent stiffness of the ribbon. Unfortunately, however, the cross-sectional area of such a round wire would be substantially less than the cross-sectional area of the ribbon configuration. Therefore the tensile integrity of the core wire would be significantly lowered. In a commonly used steerable coronary guide wire, the dimensions of the ribbon structure of the tip portion is approximately 0.001 by 0.003 inches. Such dimensions in a high tensile strength stainless steel core wire yield a tip portion with a high degree of flexibility and a tensile strength of approximately 0.9 lbs, which is close to the minimum acceptable tensile strength integrity for the tip portion of the guide wire.

While the prior art guide wire described above has a tip portion with good flexibility and acceptable tensile integrity, it does have compromised steerability as a result of the ribbon structure in the tip portion. The ribbon portion is typically about 2 cm in length. Any time the tip portion is positioned in a tortuous region of the vasculature (such as illustrated in FIG. 5), the ribbon will naturally bend only in the direction perpendicular to the ribbon's widest dimension (e.g., out of the plane of the page as shown in FIG. 2B). For a ribbon structure, there are thus only two stable bending directions 180 degrees apart from each other.

If, in this anatomical setting, the guide wire is rotated in an effort to steer the tip, the tip will resist rotating. Torque or energy will be stored in the ribbon in the form of a twist in the proximal region of the ribbon, as well as in the core wire extending proximally from the ribbon. Continued rotation of the proximal end of the guide wire will cause enough torque to build up such that the tip portion will suddenly rotate or "whip" to its next stable orientation. This orientation is 180 degrees from the previous orientation. Therefore, the ability to rotate the tip to orientations between 0 and 180 degrees is hampered. Similarly, if the guide wire is further rotated, the tip portion will again resist rotating until enough torque is built up and then the tip will suddenly rotate an addition 180 degrees.

There thus is a need for a steerable guide wire that exhibits controllable steering of the tip even in anatomically challenging vasculature. Such a steerable guide wire should have excellent steerability, tip flexibility, as well as tensile integrity. Moreover, there is a further need for a guide wire that is able to be rotated at the proximal end without any "whipping" of the distal tip.

SUMMARY OF THE INVENTION

The present invention provides for a steerable guide wire that dramatically improves steerability without compromising tensile integrity or flexibility.

In one aspect of the invention, a steerable guide wire includes a core wire having a proximal end and a distal end. A multi-filament bundle is affixed to the distal end of the core wire. An outer coil surrounds at least a portion of the core wire and the multi-filament bundle. A proximal end of the multi-filament bundle is secured to a distal end of the coil. By locating the multi-filament bundle in the distal tip portion of the guide wire, a guide wire is provided that is highly flexible, has a high degree of tensile integrity, and is highly steerable, even in tortuous vasculature.

In another aspect of the invention, a guide wire includes a proximal portion including a core wire and a distal portion that includes a multi-filament bundle coupled to the distal end of the core wire.

In yet another aspect of the invention, a guide wire includes a core wire having a proximal end and a distal end and a multi-filament bundle disposed at the distal end of the core wire, the multi-filament bundle including a plurality of filaments that are twisted in a common direction. A coil surrounds at least a portion of the core wire and the multi-filament bundle.

In one aspect of the invention, the multi-filament bundle includes a central filament and a plurality of outer filaments. In an alternative aspect of the invention, the multi-filament bundle includes a central filament surrounded by a plurality of filament bundles. Each bundle includes a plurality of individual filaments.

In one aspect of the invention, the multi-filament bundle may be made of a central filament formed from a first material and a plurality of outer filaments formed from a second material. For example, the central filament may be formed from a radiopaque material.

It is an object of the invention to provide a guide wire that is highly flexible, has a high degree of tensile integrity, and is highly steerable, even in tortuous vasculature. Additional objects of invention are discussed below with reference to the drawings and the description of the preferred embodiments.

BRIEF DESCRIPTION OF THE DRAWINGS

FIG. 1A is a side view of a guide wire according to the prior art. FIG. 1A further includes partial cross-sectional views illustrating the core wire portion under the outer coil.

FIG. 1B is a cross-sectional view of the proximal shaft portion of the guide wire taken along the line A-A of FIG. 1A.

FIG. 1C is a cross-sectional view of the mid-shaft portion of the guide wire taken along the line B-B of FIG. 1A.

FIG. 1D is a cross-sectional view of the distal tip portion of the guide wire taken along the line C-C of FIG. 1A.

FIG. 2B illustrates the width of the ribbon structure according to the prior art.

FIG. 4A illustrates a magnified view of the distal tip portion of a guide wire according to one aspect of the invention.

FIG. 4B illustrates a cross-sectional view of the distal tip portion of the guide wire taken along the line D-D in FIG. 4A according to one embodiment of the invention.

FIG. 4C illustrates a cross-sectional view of the distal tip portion of the guide wire taken along the line D-D in FIG. 4A according to another embodiment of the invention.

FIG. 4D illustrates a cross-sectional view of the distal tip portion of the guide wire taken along the line D-D in FIG. 4A according to another embodiment of the invention.

FIG. 4E illustrates a cross-sectional view of the distal tip portion of the guide wire taken along the line D-D in FIG. 4A according to another embodiment of the invention.

DETAILED DESCRIPTION OF THE PREFERRED EMBODIMENTS

Figure 2A:
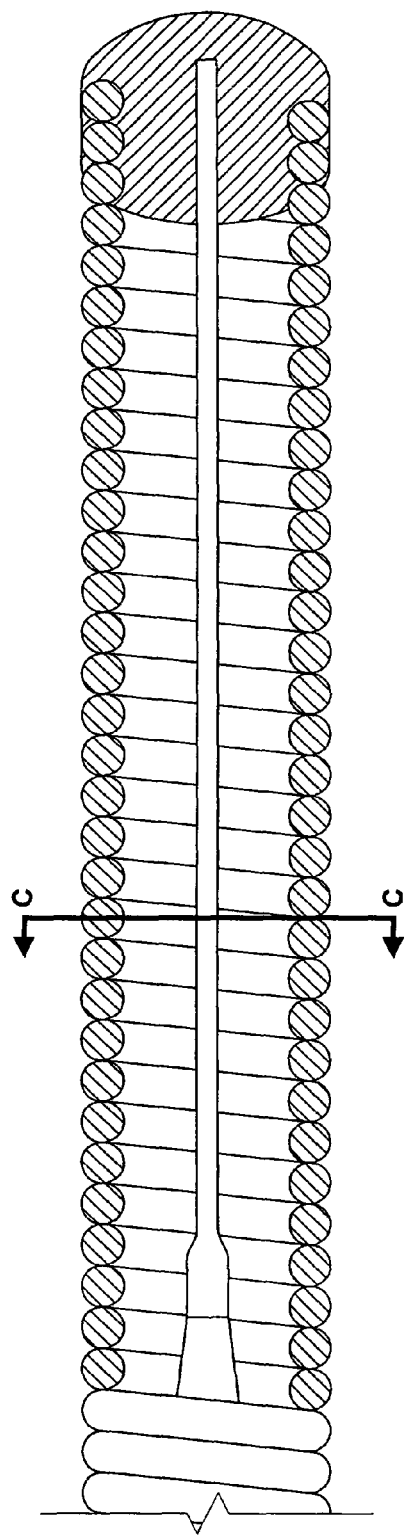
FIG. 2A is a magnified side view of the dashed region of FIG. 1A.
Figure 2B:
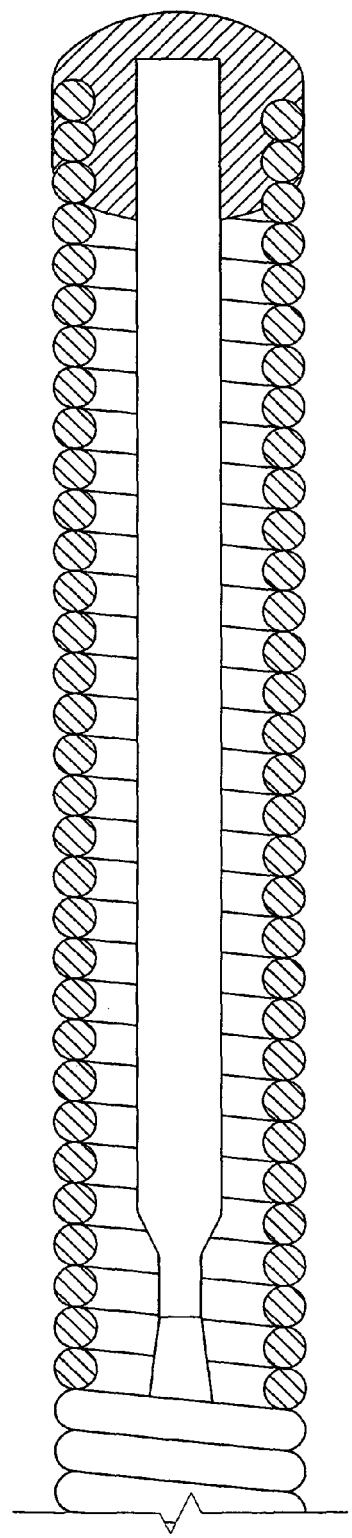
FIG. 2B is a magnified top view of the dashed region of FIG. 1A. The top view is generally perpendicular to the view shown in FIG. 2A.
Figure 3:
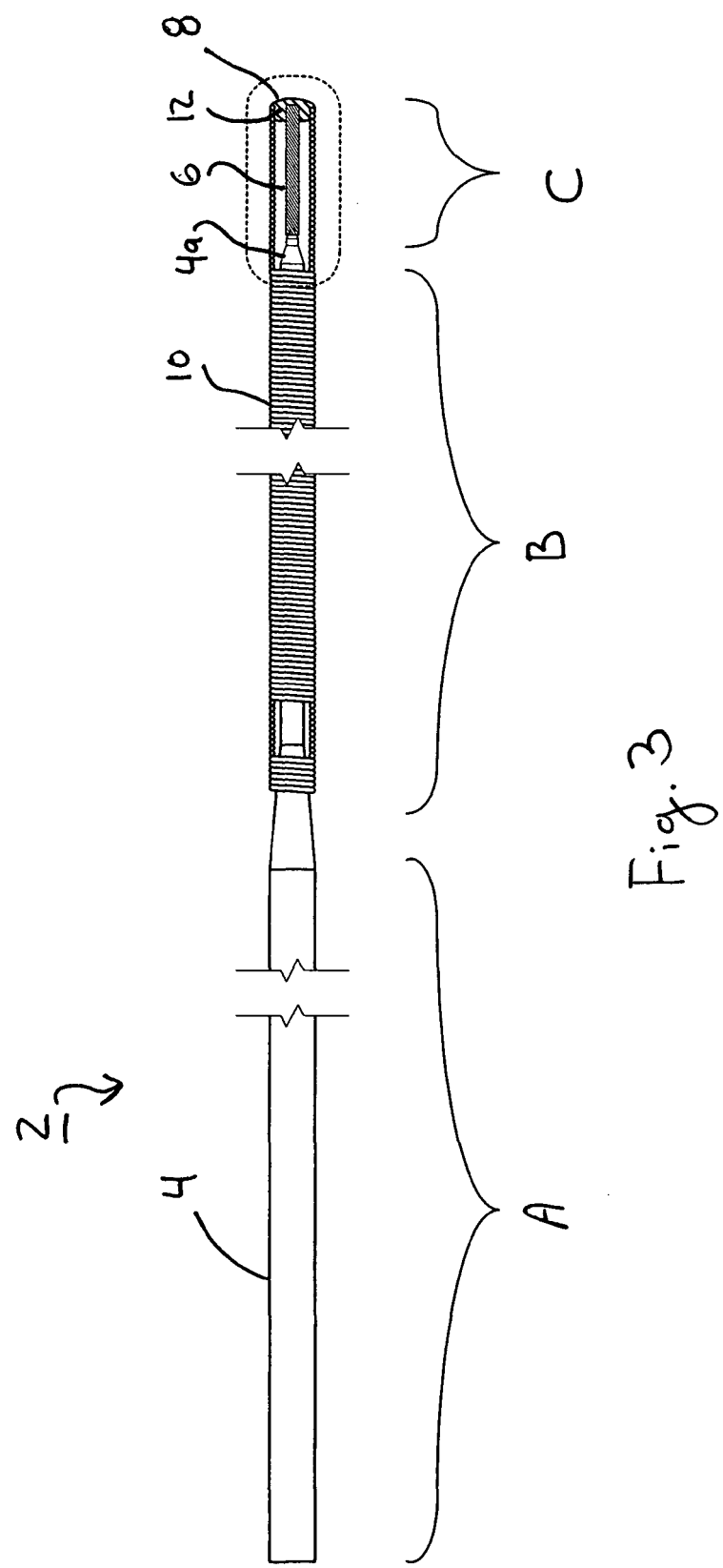
FIG. 3 illustrates side a view of a guide wire according to one aspect of the invention.

FIG. 3 illustrates a guide wire 2 according to one preferred aspect of the invention. The guide wire 2 generally includes a proximal portion A, a mid portion B, and a distal tip portion C. The guide wire 2 includes a solid core wire 4 that traverses the proximal and mid portions A, B and terminates in or near the distal tip portion C. As seen in FIG. 3, the diameter of the core wire 4 is reduced in the mid portion B of guide wire 2 to increase its flexibility. The distal end 4a of the core wire 4 is coupled to a multi-filament bundle 6. The multi-filament bundle 6 projects distally from the distal end 4a of the core wire 4 and terminates in a distal tip portion 8. The guide wire 2 further includes a coil 10 that is wrapped or wound around a portion of the exterior of the core wire 4 and multi-filament bundle 6. As seen in FIG. 3, the coil 10 begins in the mid portion B of the guide wire 2 and terminates at the distal tip 8. The distal tip 8 may include an end cap 12 such as a weld, braze, solder, adhesive, or the like to secure the distal most end of the multi-filament bundle 6.

The proximal and mid portions A, B of the guide wire 2 may be formed of any material suitable for guide wires including, but not limited to, 304 stainless steel, 316 stainless steel, NITINOL, MP35N, or ELGILOY. Fabrication of the proximal and mid portions A, B of the guide wire 2 may make use of methods and techniques such as centerless grinding and/or chemical etching. The outer coil 10 may be formed of stainless steel or other suitable materials. In one aspect of the invention, the entire outer coil 10 or one or more sections thereof can incorporate radiopaque materials such as platinum/iridium, gold, or the like. Alternatively, in place of the outer coil 10, a polymer jacket, preferably loaded with radiopaque material such as barium sulfate or bismuth subcarbonate may be secured over all or portions of the core wire 4 and multi-filament bundle 6. Moreover, the guide wire 2 may include one or more lubricious coatings (not shown) that are applied to the guide wire 2 or portions thereof.

Still referring to FIG. 3, the core wire 4 terminates at or near the distal end of the mid portion B of the guide wire 2. In one preferred aspect of the invention, a multi-filament bundle 6 is attached or otherwise mechanically connected to the distal end of the core wire 4. The multi-filament bundle 6 is shown as a distinct assembly from the core wire 4. The multi-filament bundle 6 extends to the distal tip portion 8 of the guide wire 2.

The multi-filament bundle 6 includes a plurality of individual filaments 6*a* that are arranged in a bundle, for example, as shown in FIG. 4A. In one aspect of the invention, the multi-filament bundle 6 may be formed of two or more individual wire filaments of high tensile strength material such as 304 stainless steel or 316 stainless steel or other suitable materials. In a preferred embodiment, the multi-filament bundle 6 may include stranded wire cable formed of seven wire filaments 6*a* as depicted in FIG. 4B. FIG. 4A shows a proximal end portion of the multi-filament bundle 6 extending proximal of a distal end surface of the core wire 4.

Alternatively, the multi-filament bundle 6 may be formed from three filaments 6*a* (e.g., wire filaments) as is depicted in FIG. 4C. A stranded wire cable comprising three or seven wire filaments 6*a* of the same diameter may be preferred as it is generally more structurally stable than stranded wire bundles of other numbers of wire filaments. However, the present guide wire 2 contemplates using a multi-filament bundle 6 of any number of filaments 6*a* greater than two. In addition, the multi-filament bundle 6 may be formed from a multi-filament inner core surrounded by a plurality of outer filaments.

In one aspect of the invention, the multi-filament bundle 6 includes a seven filament 6*a* stranded wire cable of high tensile strength stainless steel. The length of the multi-filament bundle 6 is preferably between 1 and 4 cm and most preferably about 2 cm although other lengths are also contemplated by the scope of the present invention. The filaments 6*a* are preferably about 0.0005 inch to 0.0015 inch diameter and most preferably about 0.0008 to 0.0010 inch diameter. For example, FIGS. 4A and 4B illustrate multi-filament bundle 6 in the form of a stranded wire bundle that is arranged with a central filament 6*a* surrounded by six outer filaments 6*a* all twisted in a common direction.

In an alternative embodiment, the multi-filament bundle 6 is formed from three filaments 6*a* as is depicted in FIG. 4C. In this embodiment, to achieve a tip portion of comparable flexibility to a guide wire 2 of the above embodiment (FIGS. 4A and 4B), the wire filaments 6*a* are preferably somewhat larger in diameter.

FIG. 4D illustrates a further embodiment wherein the central filament 6*a* is of a different dimension (i.e., diameter) than the outer filaments 6*a*'. For example, there may be a single central filament 6*a* and at least 7 outer filaments 6*a*'. FIG. 4E depicts a further alternative embodiment wherein the multi-filament bundle 6 includes one or more filament bundles 6*b*. As seen in FIG. 4E, a central filament 6*a* is surrounded by six filament bundles 6*b*. Each filament bundle 6*b* is formed from a plurality of filaments 6*a*.

Figure 5:
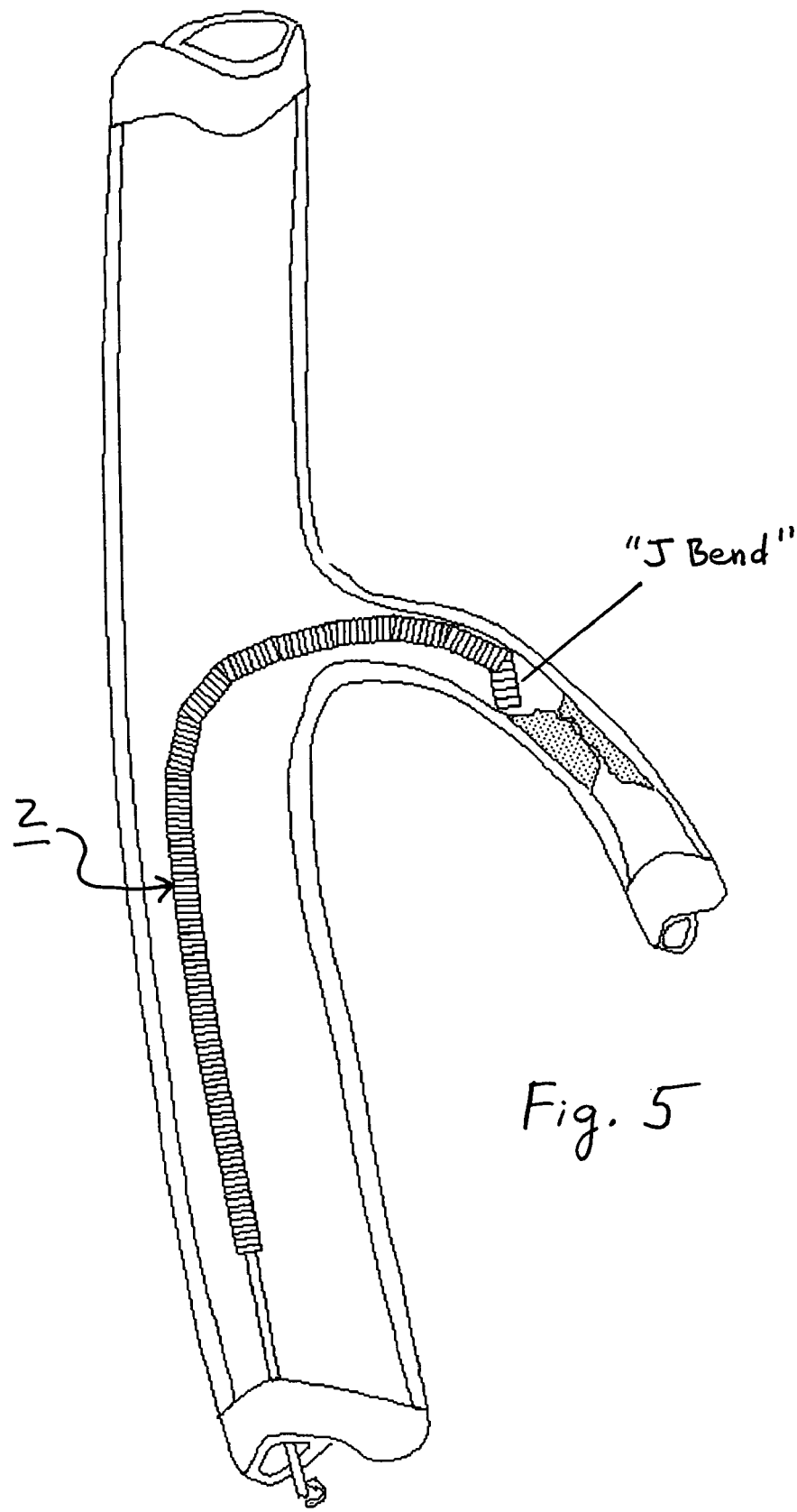
FIG. 5 illustrates a guide wire according to the present invention being advanced in a side branch of a vessel.

Each of the multi-filament bundle 6 arrangements depicted above can be tailored to have particular characteristics regarding flexibility, tensile strength, torsional stiffness, and tip formability (e.g., the ability to form a "J" bend such as that shown in FIG. 5). For instance, the arrangements depicted may incorporate one or more filaments 6*a* that are formed from different materials or have different properties than the other filament(s). By way of illustration and not limitation, in the arrangements depicted in FIGS. 4B and 4D, the central filament 6*a* may be fabricated of a radiopaque material such as platinum, while the outer filaments may be constructed of high tensile strength stainless steel. In yet another illustrative example, the central filament 6*a* could be fabricated of a more ductile material such as annealed or low tensile strength stainless steel and the outer filaments 6*a*' of high tensile strength stainless steel. This particular configuration would allow for the tip portion C to be highly formable yet retain high tensile strength due to the high tensile strength of the outer filaments 6*a*'.

In a further embodiment, the configuration depicted in FIGS. 4D and 4E may utilize high strength polymeric materials for one or more of the filaments 6*a* or filament bundles 6*b*. For example, in FIG. 4E, the central filament 6*a* could be formed of stainless steel and the outer filament bundles could be formed of a high strength polymer such as polyester, nylon, PTFE, or UHMWPE (Ultra High Molecular Weight Poly Ethylene) such as SPECTRA. The polymer bundles 6*b* could be twisted around the central filament 6*a* or, alternatively, they could be arranged in a braided configuration around central filament 6*a*.

Figure 6:
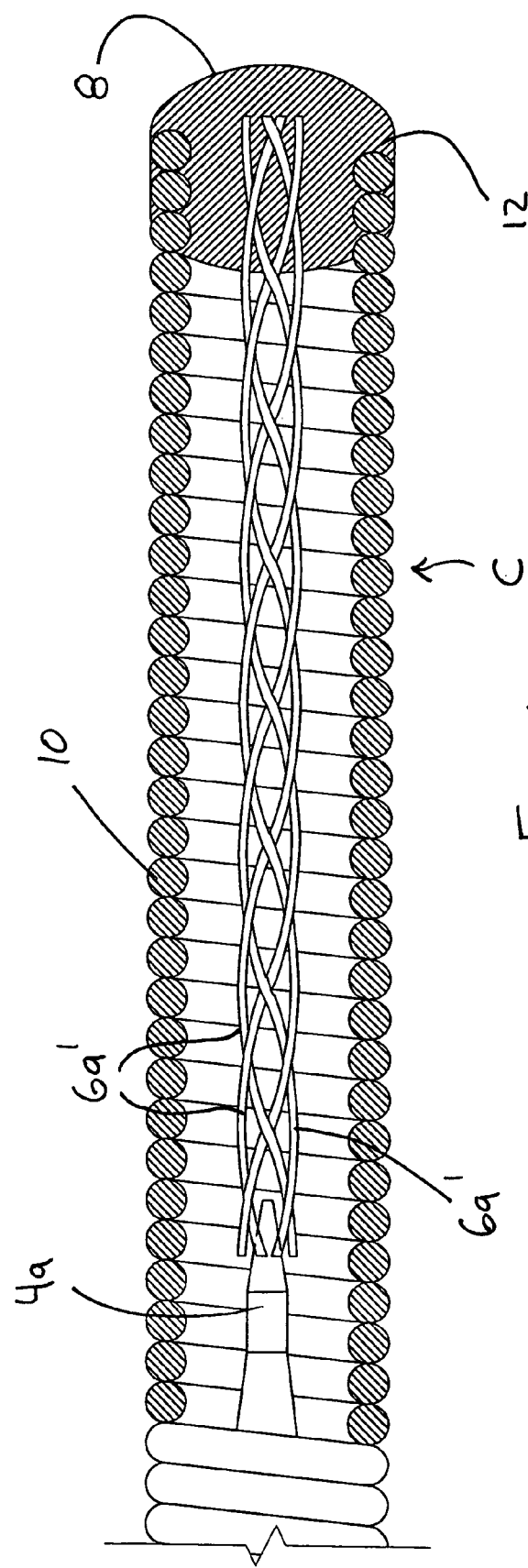
FIG. 6 illustrates a magnified view of the distal tip portion of a guide wire according to another aspect of the invention.

It is further contemplated that the arrangements depicted in FIGS. 4B and 4D could have the outer filaments 6*a*' arranged as a braid (as shown in FIG. 6). Alternatively, one or more of the outer filaments 6*a*' could be wound in a direction opposite that of the other outer filaments 6*a*' (e.g., counter-wound filaments). It is also contemplated that in the arrangements of FIGS. 4B and 4D that if the outer filaments 6*a* are in a braided configuration, there may be no central filament 6*a* as is shown in FIG. 6.

The configurations described above that make use of braided or counter-wound filaments 6*a* or filament bundles 6*b* have enhanced tortional strength. However, these configurations also have increased total or "effective" diameters. Depending on the intended application of the invention, particular configurations may be preferred.

The multi-filament bundle 6 is rotationally stable, i.e., it does not have a preferred bending direction as does the prior art ribbon configuration. Therefore, if multi-filament bundle 6 is placed in a tortuous anatomy such as that depicted in FIG. 5, the guide wire 2 will permit the distal tip 8 of the guide wire 2 to be oriented in any direction in a controllable fashion. The distal tip 8 of the guide wire 2 will advantageously have a 1:1 response or a substantially 1:1 torque response. Moreover, the guide wire 2 eliminates the "whipping" motion that heretofore accompanied guide wires that utilized a ribbon structure at the distal tip.

The attachment of multi-filament bundle 6 to the distal end 4*a* of the core wire 4 can be accomplished by any suitable means such as soldering, brazing, welding, or adhesive bonding. The distal end of the multi-filament bundle 6 can be attached to the distal end of the outer coil 10 by suitable means including soldering, brazing, welding, or adhesive bonding.

The multi-filament bundle 6 is more flexible than a solid structure of equivalent diameter, yet retains approximately the same tensile strength as a solid structure of the same equivalent diameter. This characteristic advantageously allows for a multi-filament bundle 6 to have both high flexibility and high tensile strength. However, unlike the prior art ribbon configuration, the multi-filament bundle 6 is rotationally stable. Consequently, a guide wire 2 making use of the multi-filament bundle 6 in the distal tip portion C can be highly flexible, have high tensile integrity, and be highly steerable, even in tortuous vasculature. In one preferred aspect of the invention, the distal tip 8 portion of the guide wire 2 has substantially uniform stiffness in all radial directions.

While embodiments of the present invention have been shown and described, various modifications may be made without departing from the scope of the present invention. The invention, therefore, should not be limited, except to the following claims, and their equivalents.

What is claimed is:

1. A guide wire comprising a proximal portion and a distal tip portion, the guide wire further comprising:
    a core wire having a proximal end and a distal end having a distal end surface;
    a multi-filament bundle disposed at the distal end of the core wire, the multi-filament bundle comprising a central filament distinct from the core wire and surrounded by a plurality of outer filaments, at least a portion of the plurality of outer filaments extend proximal of the distal end surface of the core wire, the multi-filament bundle being mechanically connected to the core wire, the multi-filament bundle having a proximal end and a distal region, the multi-filament bundle being rotationally stable irrespective of a particular bending direction; and
    a coil adjacent to and surrounding at least a portion of the distal end of the core wire and the multi-filament bundle;
    wherein the coil extends from the distal region of the multi-filament bundle proximally beyond the proximal end of the multi-filament bundle, and
    wherein the plurality of outer filaments are braided around the central filament,
    wherein the guide wire is operable to orient the distal tip portion in any direction in a controllable fashion to provide a substantially 1:1 torque response and the multi-filament bundle is configured to transmit torque from the core wire to the distal tip portion.

2. The guide wire of claim 1, wherein a distal end of the multi-filament bundle is secured to a distal end of the coil.

3. The guide wire of claim 1, wherein the plurality of outer filaments are braided in a diagonally overlapping pattern having one or more gaps between adjacent filaments substantially along a length of the multi-filament bundle.

4. The guide wire of claim 1, wherein the central filament is made of a first material and the plurality of outer filaments are made of a second material.

5. The guide wire of claim 4, wherein the central filament is made of a radiopaque material.

* * * * *